United States Patent
Millare et al.

(10) Patent No.: US 6,602,287 B1
(45) Date of Patent: Aug. 5, 2003

(54) STENT WITH ANTI-THROMBOGENIC COATING

(75) Inventors: Deborra Sanders Millare, San Jose, CA (US); Steven Z-H Wu, Foster City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/457,244

(22) Filed: Dec. 8, 1999

(51) Int. Cl.⁷ .................................................. A61F 2/06
(52) U.S. Cl. .................... 623/1.46; 623/1.43; 623/921; 427/2.25
(58) Field of Search .............................. 623/1.42, 1.43, 623/1.46, 921; 427/2.25, 2.24, 2.1

(56) References Cited

U.S. PATENT DOCUMENTS

| | | | |
|---|---|---|---|
| 3,288,728 A | 11/1966 | Gorham | |
| 3,839,743 A | 10/1974 | Schwarz | |

(List continued on next page.)

FOREIGN PATENT DOCUMENTS

| | | |
|---|---|---|
| CA | 2008312 | 7/1990 |
| CA | 2007648 | 4/1991 |
| CA | 1322628 | 10/1993 |
| CA | 1336319 | 7/1995 |
| CA | 1338303 | 5/1996 |
| EP | 0 380 668 A1 | 4/1989 |
| EP | 0 351 314 | 1/1990 |
| EP | 0 517 075 A1 | 12/1992 |
| EP | 0540 290 A2 | 5/1993 |
| EP | 0 565 251 A1 | 10/1993 |
| EP | 0 604 022 | 1/1994 |
| EP | 0 621 017 | 10/1994 |
| EP | 0 649 637 | 4/1995 |
| EP | 0 701 802 A1 | 3/1996 |
| EP | 0 716 836 A1 | 6/1996 |
| EP | 0 832 618 | 9/1996 |
| EP | 0 756 853 A1 | 2/1997 |
| JP | SHO 49-48336 | 12/1974 |
| JP | SHO 54-18317 | 7/1979 |
| JP | SHO 60-28504 | 7/1985 |
| JP | HEI 8-33718 | 2/1996 |
| JP | HEI 10-151190 | 6/1998 |
| WO | WO 91/17789 | 11/1991 |
| WO | WO 93/06792 | 4/1993 |
| WO | WO 95/11817 | 5/1995 |
| WO | WO 96/28115 | 9/1996 |
| WO | WO 97/10011 | 3/1997 |

OTHER PUBLICATIONS

Hollahan, et al., *Attachment of Amino Groups to Polymer Surfaces by Radiofrequency Plasmas*, Journal of Applied Polymer Science, vol. 13, pp. 807–816 (1969).

Inagaki, et al., *Hydrophilic Surface Modification of Polyethylene by No–Plasma Treatment*, Adhesion Science Technology, vol. 4, No. 2, pp. 99–107.

Gölander, et al., *RF–Plasma–Modified Polystyrene Surfaces for Studying Complement Activation*, J. Biomater. Sci. Polymer Edn., vol. 4, No. 1, pp. 25–30 (1992).

Poncin–Epaillard, et al., *Reactivity of a Polypropylene Surface Modified in a Nirtogen Plasma*, Plasma Surface Modification of Polymers, pp. 167–180 (1994).

(List continued on next page.)

Primary Examiner—Corrine McDermott
Assistant Examiner—Brian E Pellegrino
(74) Attorney, Agent, or Firm—Fulwider Patton Lee & Utecht, LLP

(57) ABSTRACT

A glycocalyx-like material is applied to a stent in order to mimic the outer surface of the cells lining arteries and veins to prevent thrombogenesis. The glycocalyx material is applied over a base layer of a fluorocarbon that is applied directly to the stent surfaces.

8 Claims, 1 Drawing Sheet

U.S. PATENT DOCUMENTS

| | | |
|---|---|---|
| 4,346,028 A | 8/1982 | Griffith |
| 4,633,873 A | 1/1987 | Dumican et al. |
| 4,656,083 A | 4/1987 | Hoffman et al. |
| 4,699,611 A | 10/1987 | Bowden |
| 4,718,907 A | 1/1988 | Karwoski et al. |
| 4,722,335 A | 2/1988 | Vilasi |
| 4,723,549 A | 2/1988 | Wholey et al. |
| 4,816,339 A | 3/1989 | Tu et al. |
| 4,877,030 A | 10/1989 | Beck et al. |
| 4,879,135 A | 11/1989 | Greco et al. |
| 4,943,346 A | 7/1990 | Mattelin |
| 4,994,298 A | 2/1991 | Yasuda |
| 5,047,050 A | 9/1991 | Arpesani |
| 5,053,048 A | 10/1991 | Pinchuk |
| 5,085,629 A | 2/1992 | Goldberg et al. |
| 5,108,755 A | 4/1992 | Daniels et al. |
| 5,116,365 A | 5/1992 | Hillstead |
| 5,156,623 A | 10/1992 | Hakamatsuka et al. |
| 5,192,311 A | 3/1993 | King et al. |
| 5,197,977 A | 3/1993 | Hoffman, Jr. et al. |
| 5,222,971 A | 6/1993 | Willard et al. |
| 5,226,913 A | 7/1993 | Pinchuk |
| 5,234,456 A | 8/1993 | Silvestrini |
| 5,234,457 A | 8/1993 | Andersen |
| 5,236,447 A | 8/1993 | Kubo et al. |
| 5,269,802 A | 12/1993 | Garber |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,304,200 A | 4/1994 | Spaulding |
| 5,306,286 A | 4/1994 | Stack et al. |
| 5,314,472 A | 5/1994 | Fontaine |
| 5,330,500 A | 7/1994 | Song |
| 5,336,518 A * | 8/1994 | Narayanan et al. ......... 427/470 |
| 5,342,348 A | 8/1994 | Kaplan |
| 5,342,621 A | 8/1994 | Eury |
| 5,356,433 A | 10/1994 | Rowland et al. |
| 5,360,443 A | 11/1994 | Barone et al. |
| 5,364,354 A | 11/1994 | Walker et al. |
| 5,370,684 A | 12/1994 | Vallana et al. |
| 5,383,927 A | 1/1995 | De Goicoechea et al. |
| 5,389,106 A | 2/1995 | Tower |
| 5,423,849 A | 6/1995 | Engelson et al. |
| 5,464,650 A | 11/1995 | Berg et al. |
| 5,562,621 A | 10/1996 | Claude et al. |
| 5,562,728 A | 10/1996 | Lazarus et al. |
| 5,571,166 A | 11/1996 | Dinh et al. |
| 5,609,629 A | 3/1997 | Fearnot et al. |
| 5,618,298 A | 4/1997 | Simon |
| 5,624,411 A | 4/1997 | Tuch |
| 5,628,755 A | 5/1997 | Heller et al. |
| 5,628,781 A | 5/1997 | Williams et al. |
| 5,637,113 A | 6/1997 | Tartaglia et al. |
| 5,688,516 A * | 11/1997 | Raad et al. .................. 604/508 |
| 5,716,406 A * | 2/1998 | Farber ........................ 604/172 |
| 5,718,726 A | 2/1998 | Amon et al. |
| 5,824,048 A | 10/1998 | Tuch |

OTHER PUBLICATIONS

Gengenbach, et al., *Evolution of the Surface Composition and topography of Perfluorinated Polymers Following Ammonia–Plasma Treatment, Plasma Surface Modification of Polymers*, pp. 123–146 (1994).

Lambert, et al., *Localized Arterial Wall Drug Delivery From a Polymer–Coated Removable Metallic Stent, Circulation*, vol. 90, No. 2 pp. 1003–1011 (Aug. 1994).

De Scheerder, et al., *Biocompatibility of Polymer–Coated Oversized Metallic Stents Implanted in Normal Porcine Coronary Arteries, Atherosclerosis*, vol. 114, pp. 105–114 (1995).

Union Carbide Technology Letter, New Busiiness Department—Parylene, Oct. 1973, No. 7 (8 pages).

Union Carbide, Electronic Materials, Parylene Products, Oct. 1973, No. 9 (23 pages).

Union Carbide Technology Letter, May 1974, No. 11 (12 pages).

Union Carbide Technology Letter, Oct. 1975, No. 15 (13 pages).

Union Carbide, Electronic Materials, Parylene Products, Mar. 1976, No. 16 (4 pages).

Eskin, et al., *Growth of Cultured Calf Aortic Smooth Muscle Cells on Cardiovascular Prosthetic Materials, Journal of Biomedical Material Research*, vol. 10, pp. 113–122 (1976).

Loeb, et al., *Parylene as a Chronically Stable, Reproducible Microelectrode Insulator*, IEEE Transactions on Biomedical Engineering, pp. 121–128 (Mar. 1977).

Union Carbide, Electronic Materials, Parylene Products, Aug. 1977, No. 18 (7 pages).

Union Carbide, Electronic Materials, Parylene Products, Oct. 1977, No. 1, Revision 2 (7 pages).

Union Carbide, Electronic Materials, Parylene Products, Oct. 1977, No. 2, Revision 1 (9 pages).

Union Carbide, Electronic Materials, Parylene Products, Oct. 1977, No. 3 (21 pages).

Union Carbide, Electronic Materials, Parylene Products, Oct. 1977, No. 4 (13 pages).

Union Carbide, Electronic Materials, Parylene Products, Oct. 1977, No. 6 (12 pages).

Union Carbide, Electronic Materials, Parylene Products, Oct. 1977, No. 7 Revision 1 (8 pages).

Union Carbide, Electronic Materials, Parylene Products, Oct. 1977, No. 8, Edited (19 pages).

Union Carbide, Electronic Materials, Parylene Products, Oct. 1977, No. 10 (50 pages).

Union Carbide, Electronic Materials, Parylene Products, Oct. 1977, No. 11 (12 pages).

Union Carbide, Electronic Materials, Parylene Products, Oct. 1977, No. 12, Revision 1 (6 pages).

Union Carbide, Electronic Materials, Parylene Products, Oct. 1977, No. 13, Revision 1 (7 pages).

Union Carbide, Electronic Materials, Parylene Products, Oct. 1977, No. 14, Revision 1 (11 pages).

Union Carbide, Electronic Materials, Parylene Products, Oct. 1977, No. 15, Revision 1 (8 pages).

Union Carbide, Electronic Materials, Parylene Products, Oct. 1977, No. 17, Revision 1 (11 pages).

ISEEE Transactions on Biomedical Engineering, vol. BME–27, No. 11, Nov. 1980 (5 pages).

Sadhir, et al., *The Adhesion of Glow–Discharge Polymers, Silastic and Parylene to Implantable Platinum Electrodes: Results of Tensile Pull Tests After Exposure to Isotonic Sodium Chloride*, vol. 2, Biomaterials, pp. 239–243 (Oct. 1981).

Hahn, et al., *Glow Discharge Polymers as Coatings for Implanted Devices*, John M. Dlaton Research Center, University of Missouri–Columbia and the Graduate Center for Materials Research, pp. 109–113 (1981).

Union Carbide, Electrode Materials, Parylene Products, Jan. 18, 1982, No. 5, Revision 4 (17 pages).

Hahn, et al., *Biocompatibility of Glow–Discharge–Polymerized Films and Vacuum–Deposited Parylene*, Journal of Applied Polymer Science: Applied Polymer Symposium 38, 55–64 (1984).

Casper, et al., *Fiber–Reinforced Absorbable Compsite for Orthopedic Surgery*, Polymeric Materials Science and Engineering, Proceedings of the ACS Division of Polymeric Materials: Science and Engineering, vol. 53, Fall Meeting 1985.

Kelly et al., *Totally Resorbable High–Strength Composite Material*, Advances in Biomedical Polymers, Edited by Charles G. Gebelein (1987).

Yuen, et al., *Tissue Response to Potential Neuroprosthetic Materials Implanted Subdurally*, Biomaterials, vol. 8, No. 8, pp. 57–62 (Mar. 1987).

Nichols, et al., *Electrical Insulation of Implantable Devices by Composite Polymer Coatings*, Dalton Research Center, University of Missouri, 1987.

Schmidt, et al., *Long–Term Implant of Parylene–C Coated Microelectrodes*, Medical & Biological Engineering and Computing, pp. 96–101 (Jan. 1988).

Olson, Parylene, *A Biostable Coating for Medical Applications*, for NOVA TRAN Parylene Coating Services (Jul. 25, 1988; Nov. 14, 1988).

Beach, et al., *Xylylene Polymers*, Encyclopedia of Polymer Science and Engineering, vol. 17, Second Edition, pp. 990–1025, 1989.

Muller, et al., *Advanced in coronary Angioplasty: Endovascular Stents*, Coronary Artery Disease, vol. 1, No. 4, Jul./Aug. 1990.

Loh, et al., *Plasma Enhanced Parylene Deposition*, Antec, pp. 1099–1103 (1991).

Gebelein, et al., *Biomedical and Dental Applications of Polymers*, Polymer Science and Technology, vol. 14, pp. 143–161 (No date).

The Parylene Press (A Publication of Specialty Coating Systems, Inc.), Winter 1992 (7 pages).

Charlson, et al., *Temperature Selective Deposition of Parylene–C*, IEEE Transactions on Biomedical Engineering, vol. 39, No. 2, pp. 202–206, (Feb. 1992).

Bull, *Parylene Coating for Medical Applications* Medical Product Manufacturing News, Mar. 1993 (2 pages).

The Parylene Press (A Publication of Specialty Coating Systems, Inc.), Spring 1993 (6 pages).

The Parylene Press (A Publication of Specialty Coating Systems, Inc.), Summer 1993 (4 pages).

*Information Regarding Parylene–C Coating for ACS Metal Stent*, In–Home Memorandum from Ed Newton to Joe Callol, Mike Clayman, Dennis Houlsby and Joe Tartaglia, Oct. 15, 1993 attaching Parylene, a Biostable Coating for Medical Application by Roger Olson.

Moody: *Vacuum Coating Ultrasonic Transducers, Sensors*, Dec. 1993 (1 page).

Parylene Conformal Coatings Specifications and Properties, Sales Brochure, Union Carbide Specialty Coating Systems (12 pages).

Parylene Environmentally Compatible Conformal Coatings for Electronic Components Assemblies and Precision Parts, Brochure, Union Carbide Electronics Division (14 pages).

Parylene and Nova Tran™ Parylene Coating Services, for Unmatched Conformal Coating Performance, Brochure, Union Carbide Specialty Coating Systems (21 pages).

Nova Tran™ Custom Coating Services, Parylene Conformal Coating, Brochure, Union Carbide (8 pages).

Parylene, a Biostable Coating for Medical Applications, Brochure, Union Carbide Specialty Systems (6 pages).

Typical Parylene Properties, Printout, Para Tech Coating Company; Lab Top® Parylene Deposition System Model 3000, Sales Brochure, Para Tech Coating Company (7 pages).

Application for U.S. Letters patent Ser. No. 08/559,931 filed Nov. 17, 1995.

Holland, Nolan B., et al., *Biomimetic Engineering of Non–Adhesive Glycocalyx–Like Surfaces Using Oligosaccharide Surfactant Polymers*, Nature, vol. 392, pp. 799–801, Apr. 23, 1998.

* cited by examiner

STENT WITH ANTI-THROMBOGENIC COATING

BACKGROUND OF THE INVENTION

This invention relates generally to expandable intraluminal vascular grafts, commonly referred to as stents, and more particularly pertains to the coating of stents in order to prevent acute thrombogenesis.

Stents are implanted within vessels in an effort to maintain the patency thereof by preventing collapse and/or impeding restenosis. Implantation of a stent is typically accomplished by mounting the stent on the expandable portion of a balloon catheter, maneuvering the catheter through the vasculature so as to position the stent at the treatment site within the body lumen, and inflating the balloon to expand the stent so as to engage the lumen wall. The stent automatically locks into its expanded configuration allowing the balloon to be deflated and the catheter to be removed to complete the implantation procedure. The use of self-expanding stents obviates the need for a balloon delivery device. Instead, a constraining sheath that is initially fitted about the stent is simply retracted once the stent is in position adjacent the treatment site.

A significant concern associated with the implantation of a stent within the vasculature is the potential for restenosis and thrombogenesis which may in fact be exacerbated by the presence of the stent. The pressure exerted by the stent on the vessel wall may increase the trauma that induces hyperplasia and the presence of the stent in the blood stream may induce a local or even systemic activation of the patient's hemostase coagulation system. Bound proteins of blood plasma, principally the adhesive proteins such albumin, fibronectin, fibrinogen and fibrin, are known to trigger coagulation. The result is typically the adhesion and aggregation of thrombocytes on the surface of the stent. These proteins include peptide structures, e.g. the RGD-peptides composed of amino acids, such as glycine, arginine and asparagine. The same structures are involved in the adhesion of thrombocytes as a consequence of receptors of the thrombocyte surface, e.g. collagen, von WilleBrand factor and fibrin interactions. The same result may arise with other biomaterials, generally of metal or plastic composition, which are inserted temporarily or implanted permanently in the patient. The deposit of blood clots on the surface of the biomaterial can result from a complex reaction of plasmatic and cellular mechanisms of coagulation that enhance and influence each other. Thus, the implantation of a stent to keep the lumen of the artery open may only hasten re-occlusion by promoting localized blood clotting and reactive inflammation. Indeed, studies indicate that stents and other untreated biomaterials can be covered with a relatively thick thrombus formation only minutes after contact with blood.

Various pharmacological agents have heretofore been used to address the problem both on a systemic as well as localized level. The latter approach is most often preferred and it has been found convenient to utilize the implanted stent for such purpose wherein the stent serves both as a support for the lumen wall as a well as delivery vehicle for the pharmacological agent. However, the metallic materials typically employed in the construction of stents in order to satisfy the mechanical strength requirements are not generally capable of carrying and releasing drugs. On the other hand, while various polymers are known that are quite-capable of carrying and releasing drugs, they generally do not have the requisite strength characteristics. Moreover, the structural and mechanical capabilities of a polymer may be significantly reduced as such polymer is loaded with a drug. A previously devised solution to such dilemma has therefore been the coating of a stent's metallic structure with a drug carrying polymer material in order to provide a stent capable of both supporting adequate mechanical loads as well as carrying and delivering drugs.

Various pharmacological agents have previously been employed to reduce or suppress thrombogenesis and various methods have been developed to load such pharmacological agents onto a stent in order to achieve the desired therapeutic effect. However, further improvement is desired both in terms of the anti-thrombogenic efficacy of materials that can be coated onto stents as well as the methods by which such materials are coated onto the stent.

SUMMARY OF THE INVENTION

The present invention overcomes the shortcomings of the prior art methods for imparting anti-thrombogenic characteristics to an implantable stent and more particularly provides a new method for coating a new anti-thrombogenic agent onto a stent. The resulting stent is deployed at the treatment site to simultaneously provide mechanical support to the lumen wall as well as to prevent thrombogenesis.

The method of the present invention requires the sequential application to a stent of a base layer and a biologically active top layer. The base layer preferably consists of a fluorocarbon coating while the active layer consists of a coating of glycocalyx or glycocalyx-like material. The fluorocarbon coating provides a sterile and carbon-rich substrate to attract and retain the glycocalyx material which in turn prevents the adhesion of proteins thereto. Glycocalyx is a naturally occurring substance that is found in the external region of the cell membrane in cells that line the walls of veins and arteries. The glycocalyx is dominated by glycosylated molecules, which direct specific interactions such as cell-cell recognition and contribute to the stearic repulsion that prevents undesirable non-specific adhesion of other molecules and cells. Bioengineered glycocalyx-like material mimics the biological characteristics of naturally occurring glycocalyx. The glycocalyx molecule as well as the molecules of bioengineered glycocalyx-type materials have a flexible backbone with two types of side chains, a sugar chain that has the anti-clotting properties and a water repellent chain. The water repellent chain attaches to the fluorocarbon coating and the sugar chain protrudes outwardly to form a dense layer that prevents the attachment of plasma proteins thereto.

These and other features and advantages of the present invention will become apparent from the following detailed description of preferred embodiments which illustrate by way of example the principles of the invention.

DETAILED DESCRIPTION OF THE PREFERRED EMBODIMENTS

The coated stent of the present invention serves to support the walls of a body lumen while preventing the formation of thrombi thereon. The present invention is not limited to any particular stent configuration or delivery method nor is the construction of the stent structure limited to the use of any particular construction material.

Figure 1:
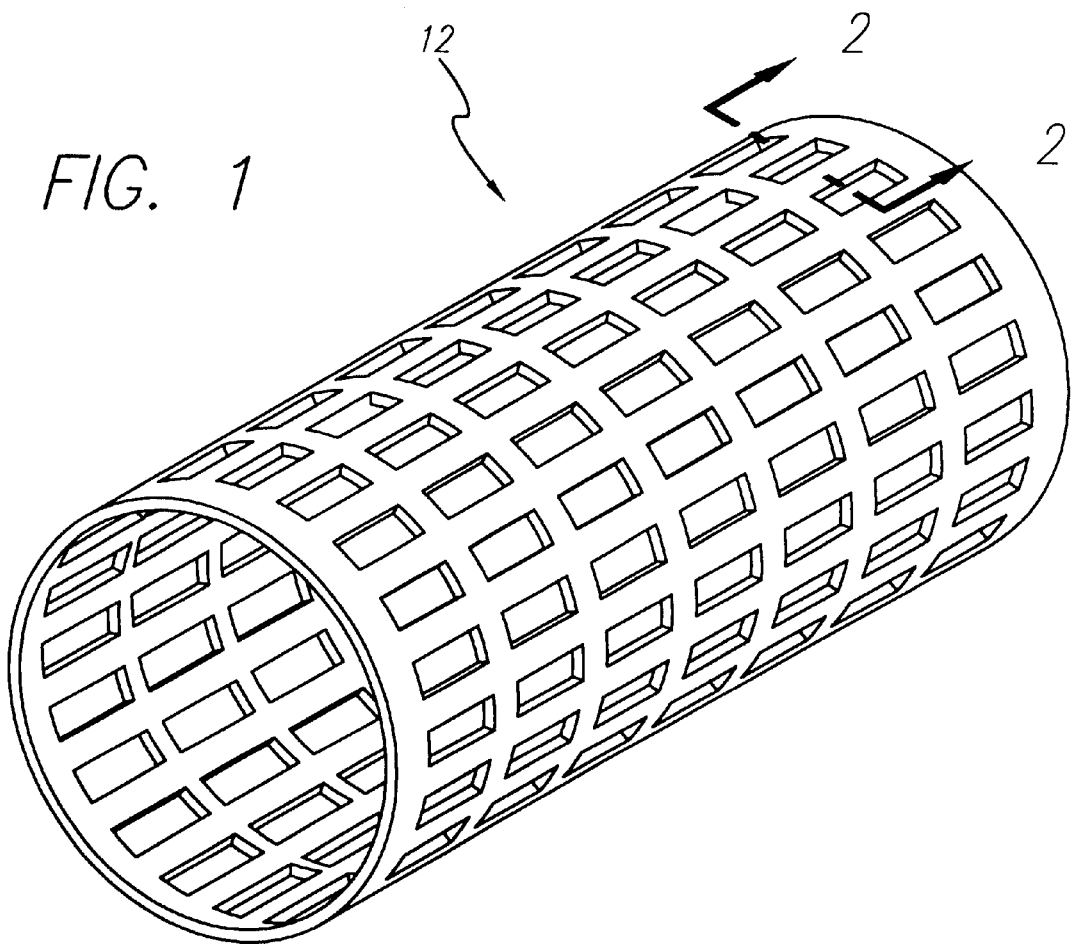
FIG. 1 is a perspective view of a coated stent of the present invention.

FIG. 1 generally illustrates a coated stent 12 of the present invention. The particular stent shown is for illustrative purposes only as virtually any stent configuration can be coated in accordance with the present invention. In fact, the coating can be applied to any device to be implanted or introduced into the body. The coating does not interfere with the stent structure or construction in any way and does not affect its deployment. All known stent designs with attendant delivery systems can benefit from the coating of the present invention.

Figure 2:
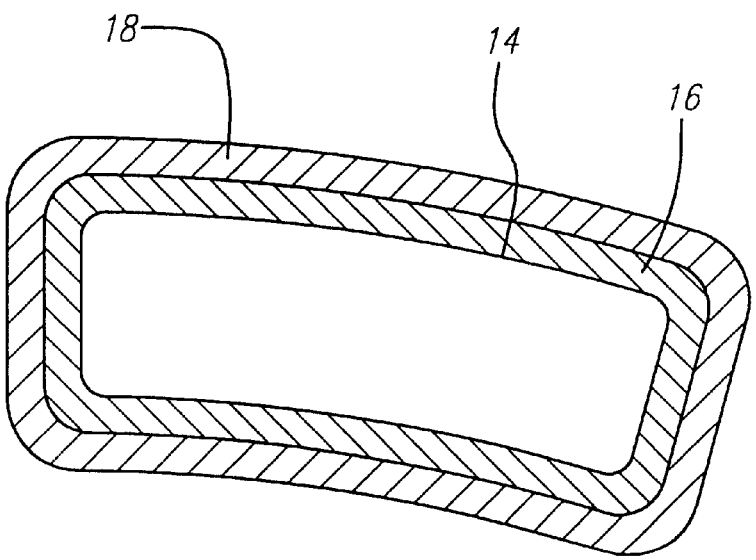
FIG. 2 is an enlarged cross-sectional view taken along lines 2—2 of FIG. 1.

FIG. 2 is an enlarged cross-sectional view of a portion of the stent shown in FIG. 1 and illustrates the two layers that are applied to the stent in accordance with the present invention. A base layer 16 is applied directly to all of the stent surfaces 14 including all of its edges. Such base layer consists of a fluorocarbon coating that positively adheres to the stent surface and avails a carbon-rich substrate for the attachment of the top layer 18 thereto. Such top layer is applied to the base-coated stent and uniformly covers all surfaces including all edges.

The fluorocarbon coating is preferred for use as a base layer in the present invention as it forms a strong bond with a variety of materials of which stents are commonly formed. Moreover, the equipment and techniques need for uniformly applying predictable amounts of a fluorocarbon to various surfaces have been well developed and are well known. The fluorocarbon provides an ideal substrate for attracting and retaining glycocalyx material as the water repellant side chains of the glycocalyx material readily attach to the carbon-rich structure of the fluorocarbon base layer. The glycocalyx material provides an ideal top layer for stent applications as the sugar side chains form a dense layer that prevents the attachment of plasma proteins. Moreover, because the exposed sugar side chains avail a surface that is very similar to surface of the cells lining the walls of the veins and arteries, the presence of the stent is effectively masked and the initiation of various defense mechanisms otherwise relied upon by the body to combat the presence of foreign materials is thereby avoided.

The coating of the stent is a multi-step process wherein the stent is first thoroughly cleaned after its fabrication. This is achieved by immersing the stent in an ultrasonic bath for 20 minutes followed by air drying. The fluorocarbon coating is preferably applied by a method known in the art as radio-frequency glow discharge (RFGD) plasma deposition. The process is performed by first securing the stent in the reactor by attaching it to a rod with a wire. The reactor is then evacuated down to a pressure of 1 milliliter. Argon gas is introduced into the reactor at a flow rate of 34.3 milliliters per minute to produce a pressure of 20 milliliter. The power is set at 80 watts and argon plasma is generated. The argon etch is applied for 30 seconds after which the power and vacuum flow is shut off and vacuum is again lowered to 1 mililiter. A fluorocarbon monomer is introduced into the reactor at a flow rate of 2 milliliters per minute. Any one of three monomers that are suitable for this application may be used, namely $C_3F_8$, $C_3F_6$ or $C_2F_6$. The monomer is applied at a pressure of 150 mililiter at a power of 20 watts for 8 to 10 minutes. The power is then turned off while the fluorocarbon monomer continues flowing for 10 minutes to quench the plasma process. The reactor is purged of fluorocarbon monomer and the reactor is returned to atmospheric pressure. The fluorocarbon coating forms a thin coating of about 0.05 microns in thickness. The stent is then placed in a sterile bag and is moved to a tissue culture hood.

After the fluorocarbon coating process has been completed, the glycocalyx-like material is applied. An appropriate glycocalyx-like material is available from researchers at Case Western Reserve University in Cleveland, Ohio. A solution is made by mixing glycocalyx-like material with dimethyl sulfoxide to make a solution concentration of between 1 and 10%. The desired concentration of glycocalyx is dependent on how thick a coating is desired. The fluorocarbon coated stent is dipped in the glycocalyx-like solution and dried at room temperature in a purified air box for 6 to 24 hours. The coated stent is then joined with the stent delivery system and is ready for deployment.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed:

1. A method for preventing thrombogenesis on a surface of an implantable medical device, comprising the steps of:

providing a medical device configured for implantation in the body;

applying a base layer of fluorocarbon material to said medical device wherein said fluorocarbon material is selected from the group consisting of $C_3F_8$, $C_3F_6$, and $C_2F_6$; and applying a glycocalyx material to said base layer, wherein said glycocalyx material includes a water repellent side chain that attaches to said fluorocarbon material and a sugar side chain that prevents the attachment of plasma proteins thereto.

2. The method of claim 1, wherein said medical device comprises a stent.

3. The method of claim 1, wherein said fluorocarbon material is applied by a radio-frequency discharge plasma deposition process.

4. The method of claim 3, wherein said fluorocarbon material is applied to a depth of about 0.05 microns.

5. The method of claim 1, wherein said glycocalyx material is applied by dipping said base layer coated medical device into a solution containing 1 to 10% of said glycocalyx material.

6. The method of claim 5, wherein said solution comprises a mixture of said glycocalyx material and dimethyl sulfoxide.

7. A stent, comprising:

an expandable structure;

a base coating of fluorocarbon material wherein said fluorocarbon material is selected from the group consisting of $C_3F_8$, $C_3F_6$, and $C_2F_6$; and a top coating of a glycocalyx material, wherein said glycocalyx material includes a water repellent side chain that attaches to said fluorocarbon material and a sugar side chain that prevents the attachment of plasma proteins thereto.

8. The stent of claim 7, wherein said base coating is about 0.05 microns thick.

* * * * *